United States Patent [19]

Higgins

[11] 4,321,999
[45] Mar. 30, 1982

[54] REUSABLE SURGICAL IMPLEMENTS HOLDER

[76] Inventor: Sam M. Higgins, 503 N. Rivershire, Conroe, Tex. 77304

[21] Appl. No.: 108,348

[22] Filed: Dec. 31, 1979

[51] Int. Cl.³ .............................................. B65D 83/10
[52] U.S. Cl. .................................. 206/370; 206/63.3; 206/380; 206/459; 206/460
[58] Field of Search ....................... 206/63.3, 380, 382, 206/383, 210, 570, 363, 364, 365, 366, 367–370, 459, 460, 447; 221/279

[56] References Cited

U.S. PATENT DOCUMENTS

| | | | |
|---|---|---|---|
| 1,054,639 | 2/1913 | Finley | 206/460 |
| 2,030,135 | 2/1936 | Carpenter | 206/447 |
| 2,142,194 | 1/1939 | Karfiol | 206/447 |
| 2,836,290 | 5/1958 | Braun | 206/460 |
| 2,940,884 | 6/1960 | White | 206/447 |
| 3,059,803 | 10/1962 | Holsinger | 206/460 |
| 3,393,688 | 7/1968 | Saverino | 221/279 |
| 3,411,978 | 11/1968 | Frohbach et al. | 206/460 |
| 3,459,297 | 8/1969 | Templeton et al. | 206/460 |
| 3,481,462 | 12/1969 | Chapel . | |
| 3,727,658 | 4/1973 | Eldridge, Jr. | 150/52 R |
| 3,819,039 | 6/1974 | Erickson . | |
| 3,861,521 | 1/1975 | Burtz | 206/63.3 |
| 3,944,069 | 3/1976 | Eldridge, Jr. | 206/350 |
| 3,948,390 | 4/1976 | Ferreri | 206/370 |
| 4,008,802 | 2/1977 | Freitag | 206/63.3 |
| 4,078,662 | 3/1978 | Volland . | |
| 4,105,115 | 8/1978 | Horvath et al. | 206/370 |
| 4,151,913 | 5/1979 | Freitag | 206/370 |
| 4,167,230 | 9/1979 | Barratt | 206/460 |

*Primary Examiner*—Joseph Man-Fu May
*Attorney, Agent, or Firm*—Gunn, Lee & Jackson

[57] ABSTRACT

In the preferred and illustrated embodiment of a holder for receiving contaminated sutures, needles, sharps and other surgical instruments used during surgical operations, a reusable holder to enable an accurate method of counting the needles used during the surgery is disclosed. The holder includes a tray, a numbered adhesive strip mounted on the tray for receiving the sutures, needles and sharps and a gathering block for pressing the adhesive strip and the surgical instruments retained thereby into an accordion-like, fan-folded package for disposal. The holder is autoclavable and may be sterilized along with the other surgical instruments in the hospital autoclave. A retractable work surface which may be used in conjunction with the holder is also disclosed. The work surface is provided with a magnetic strip for organizing sutures, needles, sharps and other surgical instruments thereon.

11 Claims, 6 Drawing Figures

U.S. Patent  Mar. 30, 1982  4,321,999
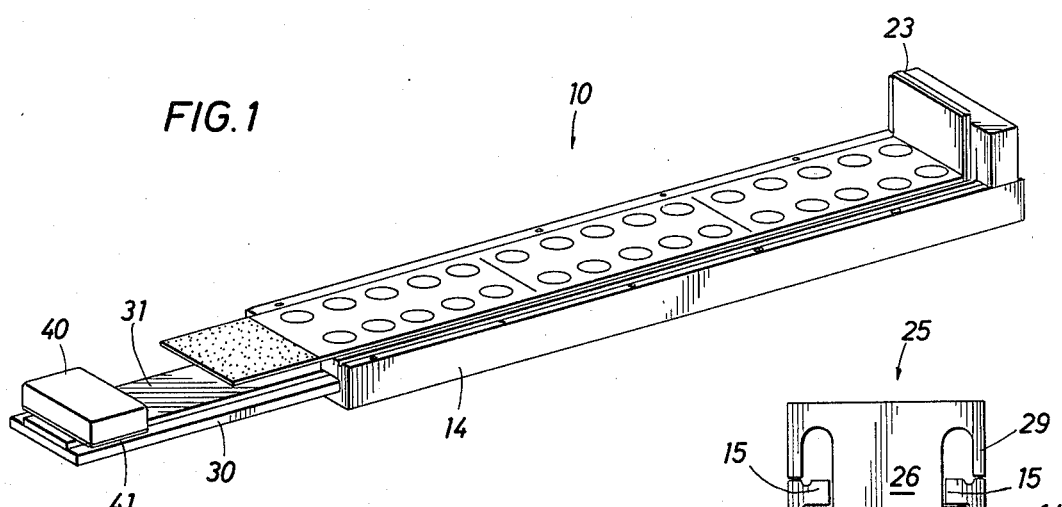
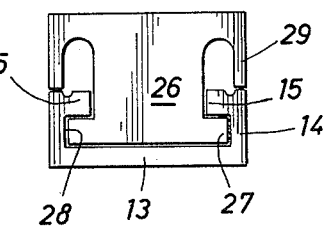
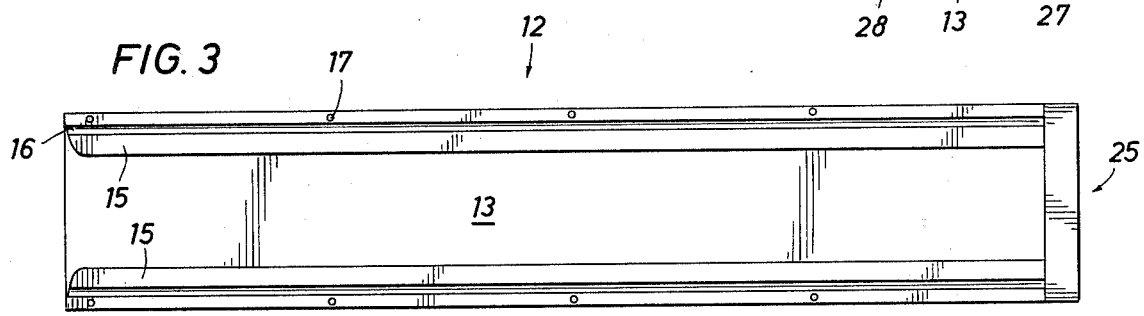
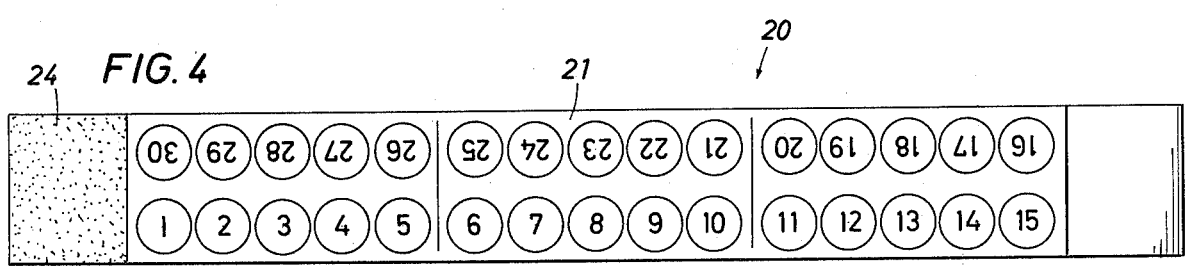
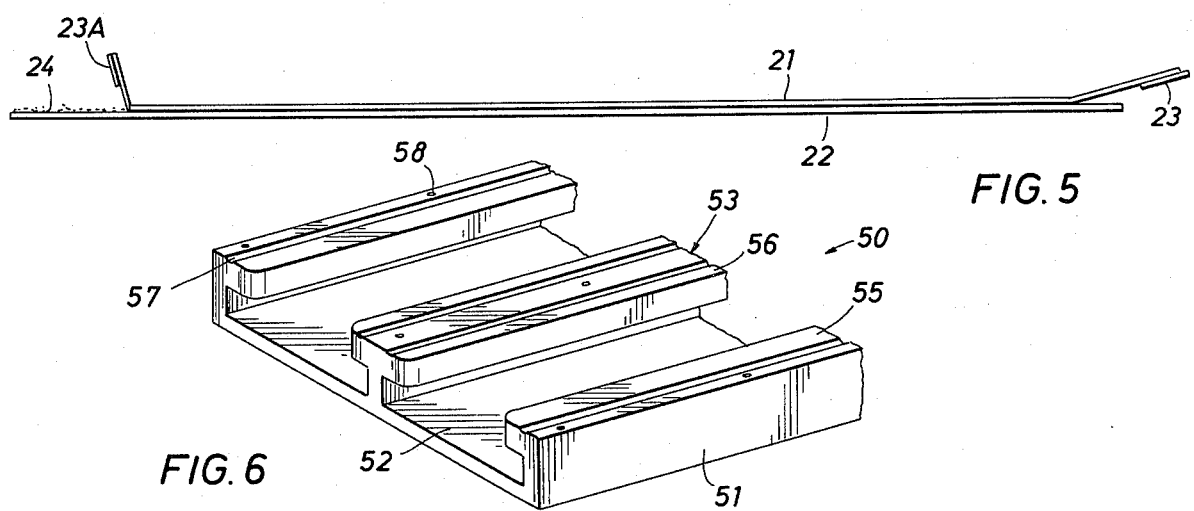

REUSABLE SURGICAL IMPLEMENTS HOLDER

BACKGROUND OF THE DISCLOSURE

This invention relates to surgical accessories and more particularly to a holder for retaining contaminated sutures, needles and other surgical instruments.

During surgical operations, a nurse or other operating room personnel is required to supply the surgeon with surgical needles, sutures and sharps as the occasion arises. An accurate count must be maintained of these instruments to insure that all needles, sutures and sharps have been removed from the patient prior to closing. The prior art discloses a number of patents directed to organization of these surgical instruments, both prior to and after being used by the surgeon. For example, U.S. Pat. No. 4,105,115 to Horvath, et al, Aug. 8, 1978; U.S. Pat. No. 4,008,802 to Freithe, Feb. 22, 1977; U.S. Pat. No. 4,151,913 to Freithe, May 1, 1979; and U.S. Pat. No. 3,727,658 to Eldridge, Jr., Apr. 17, 1973, disclose devices to organize and account for needles, sutures and sharps used during a surgical operation. However, these devices have a number of disadvantages. The devices of the prior art occupy a large surface area of the sterile space on the Mayo stand table or back table. While these devices may occupy up to 70.0 square inches of surface, they hold only ten to thirty needles. Another drawback of these prior art organizers is that some employ adhesive to secure them on the Mayo stand table or to retain the used needles. The adhesive tends to stick to anything that touches it, including the gloved hand of the nurse using the organizer or the metal needle instrument used to deposit needles or sharps in the organizer. Additionally, since these devices are lightweight and adhesively secured to the table, they are not easily repositioned to accommodate the nurse when receiving used needles and sharps from different directions or at different angular orientations, particularly when two or more surgeons are simultaneously involved in the surgery.

Some of the prioer art devices employ magnetic pads to retain needles and sharps. These magnetic pads are sensitive to any movement, and the needles and sharps become disorganized if these devices are accidentally jarred. The metal needle instrument frequently used to deposit needles in the organizer is also magnetically attracted to the magnetic pads and may disturb needles already placed in the organizer resulting in dropped and lost needles.

The foam pads, adhesive exposed pads and magnetic pads disclosed by the prior art also present a danger to the nurse placing needles in these devices. The sharp points of the needles placed in these devices remain unduly exposed so that a nurse may puncture her glove and prick her finger if not careful when placing needles on these pads. A puncture destroys the sterile condition required for the glove.

There is a desire among operating room personnel, particularly those persons responsible for the needle count, for a device which eliminates the above disadvantages of the needle count devices presently available. This invention solves the above mentioned problems by safely and accurately disposing of contaminated needles, sutures and sharps.

BRIEF SUMMARY OF THE DISCLOSURE

The present invention is directed to an instrument for receiving and counting contaminated needles, sutures and sharps. The instrument includes a channeled tray, a magnetic bar, a numbered needle receiving adhesive strip and a gathering block. The instrument is autoclavable so that it may be sterilized with the other surgical instruments by the hospital. The adhesive strip includes a metal backing so that the adhesive is not exposed and does not contact a nurse's glove or other surgical instruments.

It is, therefore, an object of the invention to provide a reusable surgical counting instrument wherein the sharp points of the needles and sharps are not exposed. This is accomplished by a feature of the invention providing a needle receiving cavity out of harm's way.

Another object of the invention is to provide an autoclavable adhesive strip for receiving the sharps and needles. This object is accomplished by providing a metal backing to the adhesive strip so that the adhesive is not exposed prior to its adhesion on the tray. The adhesive strip is provided with an embossed or printed (the terms being synonymous for this description) material having a two-row retrieving numbering system so that a nurse can review and organize the used needles at a glance. Additionally, the adhesive strip includes another feature of the invention providing a detachable tab from the metal backing having an abrasive surface for cleaning electro-surgical tips of surgical instruments.

Still another feature of the invention is to provide a retractable work surface for storing needles such as eye-needles or other instruments which are repeatedly used during surgery. This object is accomplished by providing a magnetized bar retractable within the channel cavity of the holder. Additionally, the magnetized bar may be used to retrieve small needles and other metallic objects lost in the sterile area.

Yet another object of the invention is to provide a gathering block to gather the used needles in an accordion-like package so that they may be easily counted and disposed.

BRIEF DESCRIPTION OF THE DRAWINGS

So that the manner in which the above recited features, advantages and objects of the invention, as well as others which will become apparent, are attained and can be understood in detail, a more particular description of the invention briefly summarized above may be had by reference to the embodiments thereof illustrated in the appended drawings, which drawings form a part of this specification. It is to be noted, however, that the appended drawings illustrate only typical embodiments of the invention and are not to be considered limiting of its scope, for the invention may admit to other equally effective embodiments.

FIG. 1 is a perspective view of the preferred embodiment of the invention;

FIG. 2 is an end view of the invention showing a preferred embodiment of the gathering block;

FIG. 3 is a top view of the tray of the invention; FIG. 4 is a top view of the adhesive strip of the invention;

FIG. 5 is a side view of the adhesive strip of the invention; and

FIG. 6 is a perspective view of an alternate embodiment of the tray of the invention.

DETAILED DESCRIPTION OF THE PREFERRED EMBODIMENT

Referring to FIG. 1, a suture and needle holder 10 is disclosed including a tray 12, an adhesive strip 20, a gathering block 25 and a retractable work surface 30. A pad 40 for temporarily storing reusable needles is shown attached to the work surface 30.

The tray 12, as shown in FIGS. 1 and 3, has a channel-like configuration comprising a bottom 13, two sides 14 vertically extending from the longitudinal edges of the bottom 13 and a pair of flanges 15 extending inwardly from the sides 14. The sides 14 are spaced and parallel to each other and are perpendicular to the bottom 13. The flanges 15 extend inwardly from the upper edge of the sides 14 and lie in a plane perpendicular to the sides 14 and parallel to the bottom 13. The flanges 15 are preferably an integral extension of the sides 14. Top located grooves 16 extend the longitudinal length of the flanges 15. The grooves 16 aid in aligning the adhesive strip 20 on the flanges 15. The flanges 15 also include count marks 17 spaced along the edges thereof. The count marks 17 facilitate the grouping of sharps and needles when the adhesive strip 20 is not embossed with numerals, for example, grouping five sharps or needles between two adjacent count marks 17. In this fashion, the sharps and needles may be quickly counted at a glance. The tray 12 may be fabricated from a variety of metals or plastic. The preferred construction is metal with the sides 14 bonded to the bottom 13. However, the tray 12 may be machined or extruded fom one piece of metal, or the sides 14 may be welded or brazed to the bottom 13.

Referring now to FIGS. 4 and 5, the adhesive strip 20 includes a tape-like material 21 having an adhesive on one side thereof and a metal backing 22 adhered thereto. The material 21 may be embossed with numerals for quick count of the used sharps and needles. Thirty numerals are shown embossed on the material 21 in FIG. 4; however, greater or fewer numerals may be provided, and, if desired, the numerals may be color coded. The metal backing 22 is provided to protect the material 21 during autoclaving of the surgical instruments and to prevent the adhesive from sticking to a nurse's gloved hand. One end of the material 21 is provided with a stiff metal tab 23 for the gloved nurse to grasp when peeling the material 21 from the metal backing 22 prior to adhering the material 21 onto the tray 12. A paper tab 23a is also provided at the other end of the material 21. Thus, a nurse, after peeling the material 21 from the metal backing 22, may mount the adhesive strip 20 onto the tray 12 by holding both ends of the material 21 without contacting the adhesive. At the end opposite the tab 23, the metal backing 22 includes a detachable abrasive surface 24 for cleaning the tips of electro-surgical instruments. The surface 24 may be detached from the metal backing 22 and placed on the work surface 30 to be used as needed.

The gathering block 25, as best shown in FIG. 2, is of a generally T-shaped construction of metal or plastic. The trunk 26 of the block 25 spans the space between the flanges 15. The legs 27 of the T-shaped block 25 extend outwardly from the trunk 26 and fill the channels 28 formed by the bottom 13, the sides 14 and the flanges 15. The trunk 26 and the legs 27 fit loosely within the channel cavity of the tray 12 so that the gathering block 25 may freely move in the tray 12. The upper portion of the block 25 includes downwardly extending arms 29 slightly spaced from the upper surface of the flanges 15. The arms 29 guide the gathering block 25 along the tray 12 and aid in maintaining the block 25 vertically aligned to insure that the block 25 moves smoothly within the tray 12. The gathering block 25 is approximately twice the height of the tray 12. The width of the block 25 is equal to the outside width of the tray 12. Preferably, the block 25 is approximately 0.25 inch thick, and it should be thick enough to remain stiff when force is applied thereto. The gathering block 25 is normally pushed or pulled to collect and press the material 21 and the used needles and sharps deposited therein into a locking, accordion-like, fan-folded package. The metal tab 23 may be bent around the bundled needle points and material for safely discarding the package.

The retractable work surface 30 shown in FIG. 1 is a rectangular bar approximately the length of the tray 12 and freely movable within the channels thereof. The work surface 30 includes a magnetic strip 30 about 0.50 inch in width mounted along the center thereof. The work surface 30 may be used in conjunction with the tray 12 as shown in FIG. 1 or separate therefrom. Preferably, the work surface 30 may be employed to temporarily store surgical instruments which may be repeatedly used during an operation. For example, the work surface 30 is often used in conjunction with an eye-needle disposable pad 40. The pad 40 includes a metal base 41 attachable to the magnetic strip 31. The work surface 30 may also be used to organize sterile needles, sharps and sutures on the magnetic strip 31 to be used during surgery. Occasionally, needles are dropped on the operating room floor. It is very difficult to pick up the dropped needles with a gloved hand and, of course, contaminates the sterile glove. The work surface 30 is ideal in these situations for retrieving the dropped and/or lost needles. The work surface 30 may be removed from the tray 12 and swept over the area where the needle was dropped. The magnetic strip 31 attracts the dropped needles for easy recovery thereof.

FIG. 6 shows an alternate embodiment of the tray 12 comprising a double tray 50. The tray 50 includes upstanding parallel sides 51 perpendicularly extending from a bottom 52. A central T-shaped partition 53 divides the bottom 52 to form the double tray 50. Flanges 55 extend inwardly from the sides 51. The top of the partition 53 forms opposed flanges 56 to complete the channel-like configuration of the double tray 50. The flanges 55 and 56 lie in a common plane perpendicular to the sides 51 and parallel to the bottom 52. The tray 50 includes alignment grooves 57 and counting marks 58 for the purposes previously discussed in the preferred embodiment of FIG. 3.

In summary, the present invention discloses a suture and needle holder which is reusable and autoclavable with the other surgical instruments in the hospital autoclave. The holder provides a cavity to receive the sharp points of needles and sutures, thus greatly reducing the danger of injury to operating room personnel. In addition, the holder provides a gathering block to press the needles and sutures into an accordion-like, fan-folded package for convenient and safe disposal. A magnetic bar and abrasive surface are also provided to accommodate a variety of needs of surgeons and operating room personnel, yet the holder is compact and requires very little space in the operating room.

While the foregoing is directed to the preferred embodiment of the present invention, other and further embodiments of the invention may be devised without departing from the basic concept thereof, and the scope thereof is determined by the claims which follow.

I claim:

1. A holder for surgical instruments comprising:
   (a) an elongate tray having a bottom and two spaced and upstanding sides extending therefrom, said tray being open interiorally therein and defining a channel-like cavity;
   (b) a pair of spaced flange means, said flange means being deployed along and extending from each of said sides, said flange means defining a plane spaced from and above said bottom;
   (c) an adhesive strip mountable on said flange means for retaining one or more surgical instruments; and
   (d) gathering means for pressing said adhesive strip and the instruments retained thereby into an accordion-like, fan-folded package.

2. The apparatus of claim 1 wherein said adhesive strip includes a metal backing, said adhesive strip comprising a tape-like material having numerals embossed thereon to facilitate quick counting of the surgical instruments retained by said adhesive strip and said adhesive strip including an adhesive for attachment to said flange means.

3. The apparatus of claim 2 wherein said adhesive strip includes a stiff tab at one end thereof, said tab providing a grasping surface for mounting said adhesive strip on said tray by contacting said adhesive against said flange means and further enabling handling without premature or unintended contact against said adhesive.

4. The apparatus of claim 1 wherein said gathering means is a T-shaped block slidable within the cavity of said tray.

5. The apparatus of claim 4 wherein said block is profiled to fit in conformance with said channel-like cavity and is locked thereinto, preventing refraction therefrom while moving therealong, said block profile extending above and below the plane defined by said flange means.

6. The apparatus of claim 5 wherein said block is made of plastic or metal.

7. The apparatus of claim 1 wherein said holder includes a work surface comprising an elongate, rectangular bar storable within the cavity of said tray, said work surface including a magnetic strip secured thereto.

8. The apparatus of claim 1 wherein said flange means include longitudinal alignment grooves for aligning said adhesive strip on said tray.

9. The apparatus of claim 8 wherein said flange means include spaced count marks along the longitudinal length of said flange means for grouping the surgical instruments to facilitate quick count thereof.

10. The apparatus of claim 8 wherein said grooves are located on top, exposed faces of said flange means and further wherein said grooves are coextensive in length relative to said flange means.

11. The apparatus of claim 1 wherein said tray includes a bottom and three spaced and upstanding sides extending therefrom, said tray being open interiorly therein and defining two channel-like cavities.

* * * * *

UNITED STATES PATENT AND TRADEMARK OFFICE
CERTIFICATE OF CORRECTION

PATENT NO. : 4,321,999
DATED : March 30, 1982
INVENTOR(S) : Sam M. Higgins

It is certified that error appears in the above-identified patent and that said Letters Patent is hereby corrected as shown below:

Claim 5, line 3, "refraction" should read -- retraction --.

Signed and Sealed this

Twenty-fourth Day of August 1982

[SEAL]

Attest:

GERALD J. MOSSINGHOFF

*Attesting Officer*  *Commissioner of Patents and Trademarks*